United States Patent
Calvi et al.

(10) Patent No.: US 9,394,520 B2
(45) Date of Patent: Jul. 19, 2016

(54) EXPANSION OF HEMATOPOIETIC STEM CELLS

(75) Inventors: Laura Maria Calvi, Rochester, NY (US); Regis O'Keefe, Pittsford, NY (US)

(73) Assignee: University of Rochester, Rochester, NY (US)

( * ) Notice: Subject to any disclaimer, the term of this patent is extended or adjusted under 35 U.S.C. 154(b) by 716 days.

(21) Appl. No.: 12/517,885

(22) PCT Filed: Dec. 3, 2007

(86) PCT No.: PCT/US2007/086279
§ 371 (c)(1),
(2), (4) Date: Jun. 5, 2009

(87) PCT Pub. No.: WO2008/073748
PCT Pub. Date: Jun. 19, 2008

(65) Prior Publication Data
US 2010/0322907 A1    Dec. 23, 2010

Related U.S. Application Data

(60) Provisional application No. 60/869,200, filed on Dec. 8, 2006.

(51) Int. Cl.
| | | |
|---|---|---|
| A61K 31/557 | (2006.01) | |
| A61K 35/28 | (2015.01) | |
| C12N 5/071 | (2010.01) | |
| C12N 5/077 | (2010.01) | |
| C12N 5/078 | (2010.01) | |
| C12N 5/0789 | (2010.01) | |
| A61K 39/00 | (2006.01) | |

(52) U.S. Cl.
CPC ............ *C12N 5/0647* (2013.01); *A61K 31/557* (2013.01); *A61K 35/28* (2013.01); *A61K 2039/515* (2013.01); *C12N 2501/02* (2013.01)

(58) Field of Classification Search
None
See application file for complete search history.

(56) References Cited

U.S. PATENT DOCUMENTS

| | | | | |
|---|---|---|---|---|
| 6,498,172 | B1 * | 12/2002 | Cameron et al. | ............... 514/347 |
| 8,029,780 | B2 | 10/2011 | Kollet et al. | |
| 8,241,903 | B2 | 8/2012 | Lapidot et al. | |
| 8,367,057 | B2 | 2/2013 | Lapidot et al. | |
| 2002/0142462 | A1 | 10/2002 | Ildstad et al. | |
| 2004/0248295 | A1 | 12/2004 | Nawa et al. | |
| 2005/0203086 | A1 * | 9/2005 | Constan et al. | ............ 514/227.5 |
| 2006/0247214 | A1 | 11/2006 | DeLong et al. | |
| 2006/0270721 | A1 | 11/2006 | Han et al. | |
| 2006/0270735 | A1 | 11/2006 | Deaciuc et al. | |
| 2006/0270740 | A1 | 11/2006 | Sato et al. | |

FOREIGN PATENT DOCUMENTS

| | | |
|---|---|---|
| EP | 0855389 | 7/1998 |
| EP | 1114816 | 7/2001 |
| EP | 1132086 | 9/2001 |
| WO | WO 01/12596 | 2/2001 |
| WO | WO 01/46140 | 6/2001 |
| WO | WO 01/72268 | 10/2001 |
| WO | WO 02/24647 | 3/2002 |
| WO | WO 02/42268 | 5/2002 |
| WO | WO 03/105908 | 12/2003 |
| WO | WO 2004/011484 | 2/2004 |
| WO | WO-2004035083 A2 * | 4/2004 |
| WO | WO 2004/078944 | 9/2004 |
| WO | WO-2004073591 A2 * | 9/2004 |
| WO | 2006/047569 A2 | 5/2006 |
| WO | WO 2006/127809 | 11/2006 |
| WO | WO 2007/112084 | 10/2007 |

OTHER PUBLICATIONS

Bos et al. Prostanoids and prostanoid receptors in signal transduction. Int J Biochem Cell Biol 36: 1187-1205, 2004.*
Hirata et al. Prostanoid receptors. Chemical Reviews. epub Aug. 5, 2011, pp. A-V.*
Ke et al. CP-533,536, a novel non-prostanoid EP2 receptor selective prostaglandin E2 (PGE2) agonist, stimulates local new bone formation in rats. Calcified Tissue Int. 70(4): p. 290, #p. 131, Apr. 2002.*
Harizi et al. Prostaglanin E2 modulates dendritic cell function via EP2 and EP4 receptor subtypes. J Leukoc Biol 73: 756-763, 2003.*
North et al. Prostaglandin E2 regulates vertebrate haematopoietic stem cell homeostasis. Nature 447: 1007-1012, 2007.*
Lord et al. Prostaglandin E2 Making more of your marrow. Cell Cycle 64: 3054-3057, 2007.*
"Aplastic anemia", downloaded from mayoclinic.com/health/aplastic-anemia/DS00322 on Jun. 7, 2012; 8 pages.*
"Myelodysplastic syndromes", downloaded from marrow.org/Patient/Disease_and_Treatment/About_Your_Disease/MDS/Myelodysplastic_Syndromes_(MDS).aspx on Jun. 7, 2012; 7 pages.*
Voulgarelis et al. Bone marrow histological findings in systemic lupus erythematosus with hematologic abnormalities: A clinicopathological study. Am J Hematol 81: 590-597, epub Aug. 3, 2005.*
Thanopoulos et al. Prostaglandin E2 administration in infants with ductus-dependent cyanotic congenital heart disease. Eur J Pediatrics 146: 279-282, 1987.*
Ellet et al. Zebrafish as a model for vertebrate hematopoiesis. Curr Opin Pharmacol 10: 563-570, 2010.*
Sood et al. Novel insights into the genetic controls of primitive and definitive hematopoiesis from zebrafish models. Adv Hematol 2012: 830703, 2010; 13 pages.*

(Continued)

*Primary Examiner* — Bridget E Bunner
(74) *Attorney, Agent, or Firm* — Kilpatrick Townsend & Stockton, LLP

(57) ABSTRACT

Described herein are methods, compositions and kits related to manipulating hematopoietic stem cells and more particularly to methods, compositions and kits related to increasing the number of hematopoietic stem cells in vitro and in vivo. Also described are methods, compositions and kits related to making an expanded population of hematopoietic stem cells (HSCs) and methods, compositions and kits related to using the expanded population of HSCs.

35 Claims, 12 Drawing Sheets

(56) References Cited

OTHER PUBLICATIONS

Teramura et al., Oncologist 1: 187-189, 1996.*
Territo, M., Merck Manual definition of leukopenia, neutropenia; 2 pages; accessed Dec. 4, 2015.*
Lichtin, A.E., Merck Manual definition of decreased erythropoiesis; 2 pages; accessed Dec. 4, 2015.*
Steinwall et al. ONO-8815Ly, an EP2 agonist that markedly inhibits uterine contractions in women. BJOG: Int J Obstetc Gynaecol 111: 120-124, 2004.*
Arai et al., "Tie2/angiopoietin-1 signaling regulates hematopoietic stem cell quiescence in the bone marrow niche" *Cell* 118:149-61 (2004).
Burns et al., "Hematopoietic stem cell fate is established by the Notch-Runx pathway" *Genes and Development* 19:2331-2342 (2005) Epub: Sep. 15, 2005.
Calvi et al., "Activated parathyroid hormone/parathyroid hormone-related protein receptor in osteoblastic cells differentially affects cortical and trabecular bone" *J Clin Invest* 107(3):277-286 (2001).
Calvi et al., "Osteoblastic cells regulate the haematopoietic stem cell niche" *Nature* 425(6960):841-6 (2003).
Calvi et al., "Prostaglandin E2 (PGE2) regulates osteoblastic Jagged1 and expands primitive hematopoietic cells in vivo" *Blood* 108(11, Pt. 1):30A (Nov. 2006).
Frisch et al., "Prostaglandin E2 (PGE2) regulates osteoblastic jagged 1: A putative modulator of the hematopoietic stem cell (HSC) niche" *American Society for Bone and Mineral Research (ASBMR), 28th Annual Meeting*, Philadelphia, Pennsylvania USA, Sep. 15-19, 2006 (Poster).
Ivanova et al., "A stem cell molecular signature" *Science* 298:601-4 (2002).
Karanu et al., "The notch ligand jagged-1 represents a novel growth factor of human hematopoietic stem cells" *J Exp Med* 192:1365-72 (2000).
Li et al., "The human homolog of rat Jagged1 expressed by marrow stroma inhibits differentiation of 32D cells through interaction with Notch1" *Immunity* 8:43-55 (1998).
Milner and Bigas "Notch as a mediator of cell fate determination in hematopoiesis: evidence and speculation" *Blood* 93:2431-48 (1999).
Neves et al., "Effects of delta1 and jagged1 on early human hematopoiesis: correlation with expression of notch signaling-related genes in CD34+ cells" *Stem Cells* 24:1328-1337 (2006).
North et al., "A high-throughput chemical genetic screen in zebrafish establishes that prostaglandin E2 is a potent regulator of hematopoietic stem cell formation" *4th ISSCR Annual Meeting*, Jun. 29-Jul. 1, 2006, Toronto, Ontario, Canada (Abstract) http://www.abstractonline.com/viewer/viewAbstract.asp?CKey={624A099A-AC44-4D91-B783-3B76804A67EB}&MKey={743B38D5-9EAD-49CC-B2C5-497EBCE87271}&AKey={70E49A1A-9665-43B3-8BAA-55C6A8F9A624 {&SKey={C90C1A12-8335-4BF3-A11D-CB2958C4769C}.
North et al., "Prostaglandin E2 is a potent regulator of vertebrate hematopoietic stem cell homeostasis" *Blood* 108(11 Pt.l):204A (Nov. 2006).
Ramalho-Santos et al., "Stemness: transcriptional profiling of embryonic and adult stem cells" *Science* 298:597-600 (2002).
Ramsfjell et al., "Distinct requirements for optimal growth and in vitro expansion of human CD34+CD38-bone marrow long-term culture-initiating cells (LTD-IC), extended LTC-IC, and murine in vivo long term reconstituting stem cells" *Blood* 94(12):4093-4102 (1999).
Reya et al., "Stem cells, cancer, and cancer stem cells" *Nature* 414:105-11 (2001).
Spradling et al., "Stem cells find their niche" *Nature* 414:98-104 (2001).
Varnum-Finney et al., "Pluripotent, cytokine-dependent, hematopoietic stem cells are immortalized by constitutive Notch1 signaling" *Nat Med* 6:1278-81 (2000).
Visnjic et al., "Hematopoiesis is severely altered in mice with an induced osteoblast deficiency" *Blood* 103:3258-64 (2004).
Weber et al., "Parathyroid hormone stimulates expression of the Notch ligand Jagged1 in osteoblastic cells" *Bone* 39(3):485-93 (2006). Epub May 2, 2006.
Zhang et al., "Identification of the haematopoietic stem cell niche and control of the niche size" *Nature* 425:836-41 (2003).
Jones, et al., "Stromal Expression of Jagged 1 Promotes Colony Formation by Fetal Hematopoietic Progenitor Cells", Blood, 92:1501-1511 (1998).
Yang, et al., "Identification of Lin-Sca+kit+CD34+Flt3-short-term hematopoietic stem cells capable of rapidly reconstituting and rescuing myeloablated transplant recipients", Blood, 105:2717-2723 (2005).

* cited by examiner

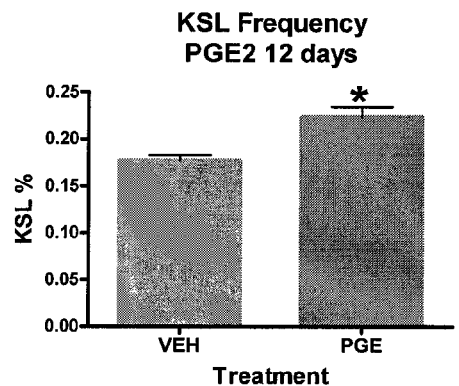
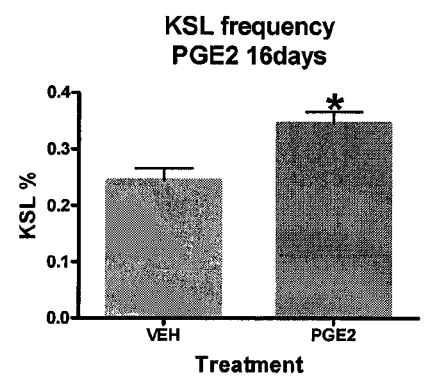
FIG. 7C
FIG. 7D
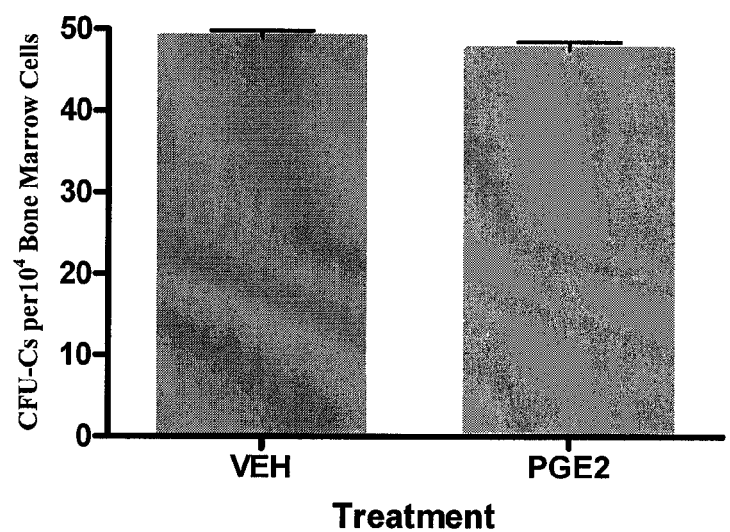
FIG. 8

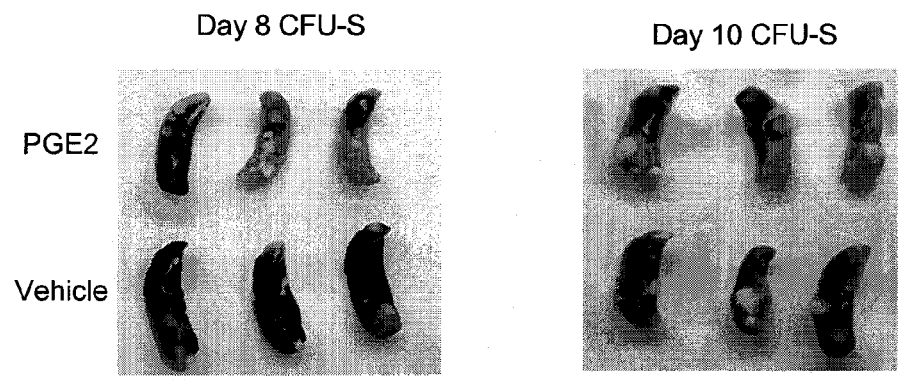
FIG. 13A
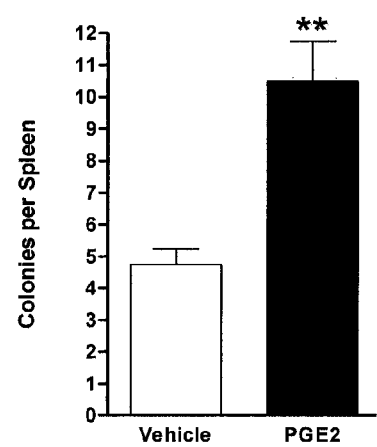 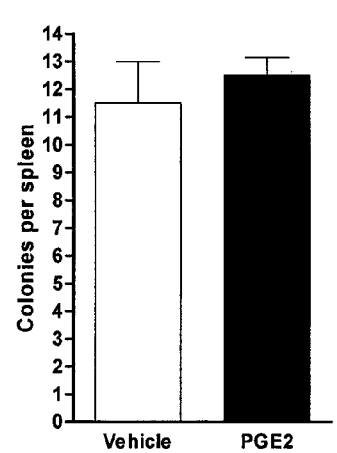
FIG. 13B      FIG. 13C

EXPANSION OF HEMATOPOIETIC STEM CELLS

CROSS-REFERENCE TO RELATED APPLICATIONS

This application claims priority to U.S. Provisional Application No. 60/869,200, filed Dec. 8, 2006, which is incorporated by reference herein in its entirety.

STATEMENT REGARDING FEDERALLY FUNDED RESEARCH

This invention was made with government support under Grant No. K08 DK064381 and Grant No. R21 DK069563 awarded by the National Institute of Health (NIH). The government has certain rights in the invention.

TECHNICAL FIELD

This invention relates to hematopoietic stem cells, and more particularly to methods, kits and compositions for manipulating hematopoietic stem cells.

BACKGROUND

Hematopoietic stem cells (HSCs) are primitive cells capable of regenerating all blood products throughout the life of an individual, balancing their self-renewal with progeny differentiation. These fundamental characteristics are in part intrinsic and in part conferred by the microenvironment or niche in which HSCs reside. Recent studies in genetically altered animals have established osteoblastic cells as important members of the HSC niche.

Hematopoietic stem cells have therapeutic potential as a result of their capacity to restore blood and immune cells in transplant recipients. Furthermore, HSCs have the potential to generate cells for other tissues such as brain, muscle and liver. Human autologous and allogeneic bone marrow transplantation methods are currently used as therapies for diseases such as leukemia, lymphoma, and other life-threatening diseases. For these procedures, a large amount of donor bone marrow must be isolated to ensure that there are enough HSCs for engraftment.

SUMMARY

Described herein are methods, compositions and kits related to manipulating hematopoietic stem cells and more particularly to methods, compositions and kits related to increasing the number of hematopoietic stem cells in vitro and in vivo. Also described are methods, compositions and kits related to making an expanded population of hematopoietic stem cells (HSCs) and methods, compositions and kits related to using the expanded population of HSCs. Optionally, the HSCs are ST-HSCs.

The details of the methods, compositions and kits are set forth in the accompanying drawings and the description below. Other features, objects, and advantages will be apparent from the description and drawings, and from the claims.

DESCRIPTION OF DRAWINGS

FIG. 1 shows increased expression of Jagged1 in UMR 106 cells.

FIG. 6 is a graph showing that PGE2 treatment has minimal effects on trabecular bone in vivo in adult male FVB/N mice treated with PGE2.

FIG. 7 shows that PGE2 treatment increased bone marrow HSC frequency in vivo. Evaluation of HSC frequency by flow cytometric analysis of the c-Kit+, Sca1+, lin− fraction (KSL) showed a trend towards an increase in KSL in bone marrow from PGE2-treated vs control mice. FIG. 7C is a graph showing KSL frequency at 12 days. FIG. 7D is a graph showing KSL frequency at 16 days.

FIG. 8 is a graph showing that intermediate progenitors of hematopoietic stem cells are not increased by PGE2 treatment. Therefore, PGE2 specifically increases HSCs. The bone marrow mononuclear cells from mice treated with vehicle and PGE2 using colony forming unit-cell (CF-C) activity in vitro. PGE2 did not increase CFU-C frequency. Peripheral white blood cell and hematocrit levels were not changed in PGE2 vs. vehicle treated mice at 16 days (WBC counts: vehicle averaged $5.75\pm0.20\times10^3$/µl; PGE2 averaged 4.72±0.61×10³/μl) (Hematocrit: vehicle averaged 42±1%; PGE2 averaged 43±2%) (n=6 for each treatment group).

FIG. 13A show CFU-S images of selected spleens after fixation. FIGS. 13B and 13C are graphs showing quantification of colonies per spleen at days 8 (FIG. 13B) and 10 (FIG. 13C) after transplantation.

DETAILED DESCRIPTION

Figure 1A:
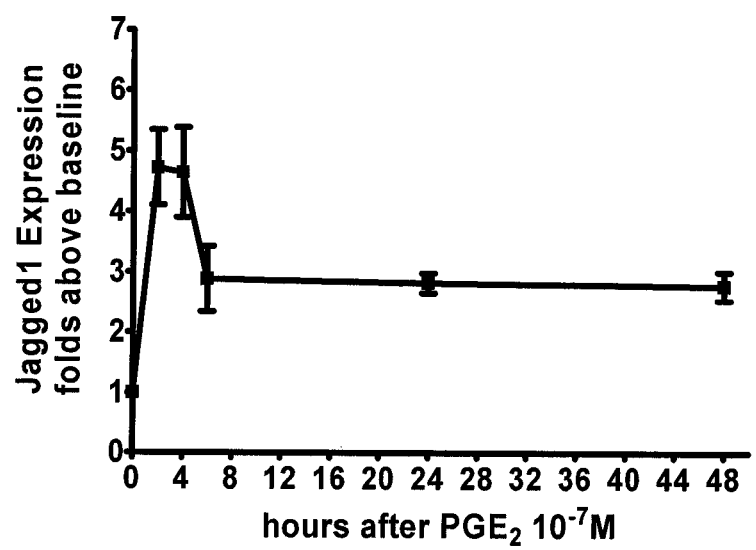
FIG. 1A shows a graph of mRNA levels over time following PGE2 exposure. UMR 106 cells were serum starved for 24 hours and then treated with a single dose of vehicle (controls) or PGE2 at a concentration of $10^{-7}$ M. RNA was collected from both control and treated samples to assess the fold change in Jagged1 mRNA by real time RT-PCR analysis corrected for by beta-actin.

Hematopoietic stem cells (HSCs) are primitive cells capable of regenerating all blood cells. During development, hematopoiesis translocates from the fetal liver to the bone marrow, which then remains the site of hematopoiesis throughout adulthood. Once hematopoiesis has been established in the bone marrow, the hematopoietic stem cells are not distributed randomly throughout the bone cavity. Instead, the hematopoietic stem cells are found in close proximity to the endosteal surfaces. The more mature stem cells (as measured by their CFU-C activity) increase in number as the distance from the bone surface increases. Finally, as the central longitudinal axis of the bone is approached terminal differentiation of mature cells occurs. Given the relationship between the hematopoietic stem cells and the endosteal surfaces of the bone, the osteoblast may play a role in hematopoiesis. Osteoblastic cells, for example, support the growth of primitive hematopoietic cells through the release of G-CSF and other growth factors.

Expanding the number of bone marrow derived stem cells is useful in transplantation and other therapies for hematologic and oncologic disease. As described in the methods herein, HSC numbers are increased in vitro, ex vivo or in vivo. A method of increasing stem cell numbers in vivo reduces the time and discomfort associated with bone marrow/peripheral stem cell harvesting and increases the pool of stem cell donors. Currently, approximately 25% of autologous donor transplants are prohibited for lack of sufficient stem cells. In addition, less than 25% of patients in need of allogeneic transplant can find a histocompatible donor. Umbilical cord blood banks currently exist and cover the broad racial makeup of the general population, but these banks are currently restricted to use in children due to inadequate stem cell numbers in the specimens for adult recipients. A method to increase stem cell numbers permits cord blood to be useful for adult patients, thereby expanding the use of allogeneic transplantation.

Accordingly, a method for increasing the number of hematopoietic stem cells is provided. An in vivo method involves administering a prostaglandin or a prostaglandin receptor agonist to the subject in an amount effective and for a sufficient period of time to increase the number of hematopoietic stem cells in the subject. For example, the prostaglandin or prostaglandin receptor agonist is administered to a subject at least about once or twice daily for at least about five, six, seven or eight days. Continuous infusion is not necessary to achieve the desired result but can be used. As used herein, an increase in HSCs means that the subject has at least one more HSC, a 10% increase, a 20% increase, a 30% increase or greater. The increase in the number of HSCs after administration of a prostaglandin or prostaglandin receptor agonist is as compared to the number of HSCs prior to administration of the prostaglandin or prostaglandin receptor agonist in the same subject or in a control subject or subjects. Preferably, the prostaglandin or prostaglandin receptor agonist activates protein kinase A (PKA) or induces expression of Jagged1 or both. Thus, a method for increasing the number of hematopoietic stem cells in a subject comprising administering Jagged1 or a PKA activator to the subject is also described.

Methods for making an expanded population of hematopoietic stem cells (HSCs) are provided comprising administering a prostaglandin or a prostaglandin receptor agonist to an unexpanded population of HSCs or to a mixture of HSCs and HSC supporting cells under conditions that allow the unexpanded population of HSCs to increase in number to form an expanded population of hematopoietic stem cells. As used herein an expanded population of HSCs refers to a population of HSCs comprising at least one more HSC, 10% more, 20% more, 30% more or greater as compared to the number of HSCs prior to or in the substantial absence of administration of the prostaglandin or prostaglandin receptor agonist in a control subject. An unexpanded population of HSCs refers to an HSC population prior to or in the substantial absence of exposure to an exogenous prostaglandin or prostaglandin receptor agonist. An unexpanded population of HSCs and HSC supporting cells refers to an HSC population and HSC supporting cells prior to or in the substantial absence of exposure to an exogenous prostaglandin or prostaglandin receptor agonist. The administering step can occur in vitro, ex vivo or in vivo. Preferably, the prostaglandin or prostaglandin receptor agonist activates protein kinase A (PKA). Optionally, the prostaglandin or prostaglandin receptor agonist induces expression of Jagged1. The HSCs are obtained from any subject and thus, are autologous or heterologous donor material. Optionally, the stem cells are human stem cells.

Optionally, the expanded population of HSCs comprises ST-HSCs. The expanded population of HSCs, for example, comprises 100% HSCs, 90% HSCs, 80% HSCs, 70% HSCs, 60% HSCs, 50% HSCs, or any amount in between. Optionally, the expanded population of HSCs comprises less than 50% HSCs. Thus, provided herein is a method of selectively expanding ST-HSCs. Specifically increasing ST-HSCs is performed in vitro or in vivo. As discussed above, an in vivo method involves administering a prostaglandin or a prostaglandin receptor agonist to the subject in an amount effective and for a sufficient period of time to increase the number of ST-HSCs in the subject. Optionally, the prostaglandin is Prostaglandin $E_2$ (PGE2). Since, as discussed in more detail below, ST-HSCs are highly proliferative, by increasing ST-HSCs in, for example, a bone marrow transplant recipient or by providing ST-HSCs to the recipient, the time period of recovery of the recipient should be reduced. Similarly, for bone marrow donors, an increase in ST-HSCs by administering a prostaglandin or prostaglandin receptor agonist to the donor before or after acquisition of the donor marrow would increase the number of ST-HSCs available for transplantation or would speed recovery of the donor, respectively. Methods for making an expanded population of ST-HSCs are also provided. For example, the method comprises administering a prostaglandin, (e.g., PGE2) or a prostaglandin receptor agonist to an unexpanded population of HSCs or to a mixture of HSCs and HSC supporting cells under conditions that allow the ST-HSCs to increase in number to form an expanded population of ST-HSCs. The unexpanded population of HSCs optimally comprises a mixed population of ST-HSCs and LT-HSCs, with or without HSC supporting cells. ST-HSCs are increased in, for example, cord blood, which is currently restricted to use in children due to inadequate stem cell numbers in the cord blood specimens for adult recipients. Thus, provided is a method of specifically increasing ST-HSCs in cord blood by contacting cord blood with a prostaglandin (e.g., PGE2) or a prostaglandin receptor agonist under conditions that increase ST-HSC number.

The expanded population of stem cells are harvested, for example, from a bone marrow sample of a subject or from a culture. Harvesting hematopoietic stem cells is defined as the dislodging or separation of cells. This is accomplished using a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded generating even larger populations of HSCs and differentiated progeny.

A method for making an expanded population of hematopoietic stem cells comprises contacting Jagged1 with an unexpanded population of cells comprising a mixture of HSCs and HSC supporting cells. The administration step occurs in vitro, ex vivo or in vivo.

As described herein, the expanded population of hematopoietic stem cells are optionally administered to a subject. Optionally, the expanded population of HSCs comprises ST-HSCs. Thus, provided are methods of providing an expanded population of hematopoietic stem cells to a subject comprising administering to the subject the expanded population of hematopoietic stem cells described herein or made by the methods described herein. Preferably, the prostaglandin or prostaglandin receptor agonist activates protein kinase A (PKA). Thus, methods for making an expanded population of hematopoietic stem cells comprise administering an agent that activates protein kinase A (PKA) to an unexpanded population of HSCs or a mixture of HSCs and HSC supporting cells under conditions that allow the unexpanded population of HSCs to increase in number to form an expanded population of HSCs.

The expanded population of HSCs or ST-HSCs are optionally used to make blood cells. Thus, methods are provided for making blood cells comprising differentiating hematopoietic stem cells into blood cells, wherein the HSCs are derived from the expanded population of HSCs as described or according to the methods as described herein. The blood cells are optionally administered to a subject in need. Optionally, the subject is the same subject from which the unexpanded population of HSCs or mixture of HSCs and HSC supporting cells was derived.

Hematopoietic stem cells as used herein refer to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). Hematopoietic stem cells are interchangeably described as stem cells throughout the specification. It is known in the art that such cells may or may not include $CD34^+$ cells. $CD34^+$ cells are immature cells that express the CD34 cell surface marker. CD34+ cells are believed to include a subpopulation of cells with the stem cell properties defined above. It is well known in the art that hematopoietic stem cells include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage. In addition, HSCs also refer to long term HSC (LT-HSC) and short term HSC (ST-HSC). LT-HSC and ST-HSC are differentiated, for example, based on their cell surface marker expression. LT-HSC are CD34−, SCA-1+, Thy1.1+/lo, C-kit+, lin−, CD135−, Slamf1/CD150+, whereas ST-HSC are CD34+, SCA-1+, Thy1.1+/lo, C-kit+, lin−, CD135−, Slamf1/CD150+, Mac-1 (CD11b)lo ("lo" refers to low expression). In addition, ST-HSC are less quiescent (i.e., more active) and more proliferative than LT-HSC. However, LT-HSC have unlimited self renewal (i.e., they survive throughout adulthood), whereas ST-HSC have limited self renewal (i.e., they survive for only a limited period of time). Any of these HSCs can be used in any of the methods described herein. Optionally, ST-HSCs are useful because they are highly proliferative and thus, quickly increase the number of HSCs and their progeny.

Hematopoietic stem cells are optionally obtained from blood products. A blood product includes a product obtained from the body or an organ of the body containing cells of hematopoietic origin. Such sources include unfractionated bone marrow, umbilical cord, peripheral blood, liver, thymus, lymph and spleen. All of the aforementioned crude or unfractionated blood products can be enriched for cells having hematopoietic stem cell characteristics in a number of ways. For example, the more mature, differentiated cells are selected against, via cell surface molecules they express. Optionally, the blood product is fractionated by selecting for $CD34^+$ cells. $CD34^+$ cells include a subpopulation of cells capable of self-renewal and pluripotentiality. Such selection is accomplished using, for example, commercially available magnetic anti-CD34 beads (Dynal, Lake Success, N.Y.). Unfractionated blood products are optionally obtained directly from a donor or retrieved from cryopreservative storage.

As discussed above, administration of the prostaglandin, prostaglandin receptor agonist or a combination thereof activates protein kinase A (PKA), induces expression of Jagged1 or both. Activation of PKA, increased expression of Jagged1 or both occurs in an HSC itself, in an HSC supporting cell or both. As used herein, the term HSC supporting cell refers to cells naturally found in the vicinity of one or more HSCs such that factors released by HSC supporting cells reach the HSC by diffusion, for example. HSC supporting cells include, but are not limited to, lymphoreticular stromal cells. Lymphoreticular stromal cells as used herein include, but are not limited to, all cell types present in a lymphoid tissue which are not lymphocytes or lymphocyte precursors or progenitors. Thus, lymphoreticular stromal cells include, osteoblasts, epithelial cells, endothelial cells, mesothelial cells, dendritic cells, splenocytes and macrophages. Lymphoreticular stromal cells also include cells that would not ordinarily function as lymphoreticular stromal cells, such as fibroblasts, which have been genetically altered to secrete or express on their cell surface the factors necessary for the maintenance, growth or differentiation of hematopoietic stem cells, including their progeny. Lymphoreticular stromal cells are optionally derived from the disaggregation of a piece of lymphoid tissue. Such cells are capable of supporting in vitro or in vivo the maintenance, growth or differentiation of hematopoietic stem cells, including their progeny. By lymphoid tissue it is meant to include bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue as used herein includes, but is not limited to, tissues such as thymus, spleen, liver, lymph node, skin, tonsil, adenoids and Peyer's patch, and combinations thereof.

Lymphoreticular stromal cells provide the supporting microenvironment in the intact lymphoid tissue for the maintenance, growth or differentiation of hematopoietic stem cells, including their progeny. The microenvironment includes soluble and cell surface factors expressed by the various cell types which comprise the lymphoreticular stroma. Generally, the support which the lymphoreticular stromal cells provide is characterized as both contact-dependent and non-contact-dependent.

Lymphoreticular stromal cells, for example, are autologous (self) or non-autologous (non-self, e.g., heterologous, allogeneic, syngeneic or xenogeneic) with respect to hematopoietic stem cells. Autologous, as used herein, refers to cells from the same subject. Allogeneic, as used herein, refers to cells of the same species that differ genetically. Syngeneic, as used herein, refers to cells of a different subject that are genetically identical to the cell in comparison. Xenogeneic, as used herein, refers to cells of a different species. Lymphoreticular stroma cells are obtained, for example, from the lymphoid tissue of a human or a non-human subject at any time after the organ/tissue has developed to a stage (i.e., the maturation stage) at which it can support the maintenance, growth or differentiation of hematopoietic stem cells. The lymphoid tissue from which lymphoreticular stromal cells are derived usually determines the lineage-commitment hematopoietic stem cells undertake, resulting in the lineage-specificity of the differentiated progeny.

The co-culture of hematopoietic stem cells (and progeny thereof) with lymphoreticular stromal cells, usually occurs under conditions known in the art (e.g., temperature, $CO_2$ and $O_2$ content, nutritive media, duration, etc.). The time sufficient to increase the number of cells is a time that can be easily determined by a person skilled in the art, and varies depending upon the original number of cells seeded. The amounts of hematopoietic stem cells and lymphoreticular stromal cells initially introduced (and subsequently seeded) varies according to the needs of the experiment. The ideal amounts are easily determined by a person skilled in the art in accordance with needs.

As used throughout, by a subject is meant an individual. Thus, subjects include, for example, domesticated animals, such as cats and dogs, livestock (e.g., cattle, horses, pigs, sheep, and goats), laboratory animals (e.g., mice, rabbits, rats, and guinea pigs) mammals, non-human mammals, primates, non-human primates, rodents, birds, reptiles, amphibians, fish, and any other animal. The subject is optionally a mammal such as a primate or a human.

The subject referred to herein is, for example, a bone marrow donor or an individual with or at risk for depleted or limited blood cell levels. Optionally, the subject is a bone marrow donor prior to bone marrow harvesting or a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment such as chemotherapy. The subject, optionally, has a decreased blood cell level or is at risk for developing a decreased blood cell level as compared to a control blood cell level. As used herein the term control blood cell level refers to an average level of blood cells in a subject prior to or in the substantial absence of an event that changes blood cell levels in the subject. An event that changes blood cell levels in a subject includes, for example, anemia, trauma, chemotherapy, bone marrow transplant and radiation therapy. For example, the subject has anemia or blood loss due to, for example, trauma. The prostaglandin or prostaglandin receptor agonist is administered to the subject, for example, before, at the same time, or after chemotherapy, radiation therapy or a bone marrow transplant. The subject optionally has depleted bone marrow related to, for example, congenital, genetic or acquired syndrome characterized by bone marrow loss or depleted bone marrow. Thus, the subject is optionally a subject in need of hematopoeisis. Optionally, the subject is a bone marrow donor or is a subject with or at risk for depleted bone marrow.

Hematopoietic stem cell manipulation is useful as a supplemental treatment to chemotherapy or radiation therapy. For example, hematopoietic stem cells are localized into the peripheral blood and then isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, as described herein, HSCs or blood cells made by the methods described herein are optionally administered to such subjects in need of additional blood cells.

Prostaglandins and Prostaglandin Receptor Agonists

The compositions described herein contain at least one prostaglandin or prostaglandin receptor agonist or combinations thereof. The term prostaglandin receptor agonists relate to the class of naturally occurring prostaglandins and to derivatives and analogues thereof, either natural or synthetic, which have the desired biological effects of naturally occurring prostaglandins. Also comprised within the term are pharmaceutically acceptable derivatives and salts of such prostaglandins or prostaglandin receptor agonists. For example, the prostaglandin is Prostaglandin $E_2$ (PGE2) or a derivative or analog thereof.

Prostaglandins and derivatives thereof are known in the art (e.g., see U.S. Publication Nos. 2006/0270735 and 2006/0270740). Prostaglandins are twenty carbon (C20) fatty acid derivatives and are a diverse family of hormone-like molecules derived from prostanoic acid. The prostaglandin family is further subdivided according to the structure of the five membered ring, such that there are the A-series (PGA), B-series (PGB), C-series (PGC), D-series (PGD), E-Series (PGE) F-series (PGF) and J-series (PGJ) of prostaglandins. In addition, prostaglandin nomenclature reflects the number of unsaturated carbon-carbon bonds in the side chains. Thus, a molecule having two double bonds is given the subscript 2, e.g., $PGE_2$. As used herein PGE2 and $PGE_2$ are used interchangeably.

Analogues and derivatives of prostaglandins include, without limitation, modifications to the alkyl side chains, such as alkyl substitutions (e.g. methyl, dimethyl, ethyl, etc.) and the level of saturation or unsaturation of the side chains. Derivatives and analogues optionally contain modified groups such as (substituted) phenyl and phenoxy. Synthetic or natural analogues and derivatives of prostaglandins have physiological properties that are generally similar to those of natural prostaglandins. However, such analogues and derivatives optionally exhibit properties that are enhanced or otherwise modified in a particular aspect, for instance, improved physiological activity or increased chemical stability. Pharmaceutically acceptable salt and ester derivatives are optionally modified at any suitable position, such as at the oxygen atom of an available hydroxyl or carboxyl group.

Natural prostaglandins (PGs) and numerous derivatives of PGs have been synthesized and their bioactivities have been studied. PGs exert their effects by binding to their receptors. PG derivatives with similar structure substituted with halogen at the 9-position, such as described in International Publication No. WO01/12596, are PG receptor agonists with activity similar to that of PG derivatives. Prostaglandin derivatives also include 2-decarboxy-2-phosphinico prostaglandin derivatives such as described in U.S. Publication No. 2006/0247214.

Prostaglandins bind to prostaglandin receptors. These receptors are members of the superfamily of seven transmembrane domain G-coupled receptors. Prostaglandin agonists activate the receptors to which they bind, thereby producing biological effects.

Prostaglandin receptor agonists useful in the methods described herein include, but are not limited to, prostaglandin E2 receptor-1 (EP-1) agonist, prostaglandin E2 receptor-2 (EP-2) agonist, prostaglandin E2 receptor-3 (EP-3) agonist and prostaglandin E2 receptor-4 (EP-4) agonist. EP-1 agonists, include, but are not limited to, ONO-D1-004, and 17-phenyl-omega-trinor-PGE2. EP-2 agonists include, but are not limited to, butaprost, ONO-8815Ly and ONO-AE1-259. EP-3 agonists include, but are not limited to, ONO-NT012, 11-deoxyPGE1 and ONO-AE-248. EP-4 agonists include, but are not limited to, AH23848, 11-deoxyPGE1 and ONO-AE1-329. EP4 receptor agonists also include EP4 receptor agonists described in U.S. Publication No. 2006/0270721, WO 02/24647, WO 02/42268, EP 1132086, EP 855389, EP 1114816, WO 01/46140 and WO 01/72268.

Prostaglandin receptor agonists also include carbocyclic $PGI_2$, a PPAR agonist, fluprostenol, a PGF receptor agonist, cloprostenol.sodium, a PGF receptor agonist, 16,16-dimethyl-prostaglandin $E_2$, a PGE receptor agonist more selective for EP-1 than EP-2,17-Phenyl-trinor-prostaglandin $E_2$, an EP-1 agonist and U-46619, a thromboxane $A_2$ receptor agonist. Combinations of the prostaglandins, prostaglandin derivatives and analogs and prostaglandin receptor agonists are used in any of the methods described herein as needed or desired.

Pharmaceutical Compositions

Provided are pharmaceutical compositions comprising one or more prostaglandins or prostaglandin receptor agonists or combinations thereof and a least one pharmaceutically acceptable excipient or carrier. By pharmaceutically acceptable is meant a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

The compositions are formulated in any conventional manner for use in the methods described herein. Administration is via any route known to be effective by one of ordinary skill. For example, the compositions is administered orally, parenterally (e.g., intravenously), by intramuscular injection, by intraperitoneal injection, transdermally, extracorporeally, intranasally or topically.

For oral administration, the compositions take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets are coated by methods well known in the art. Liquid preparations for oral administration take the form of, for example, solutions, syrups or suspensions, or they may be presented as a dry product for constitution with water or other suitable vehicle before use. Such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations optionally contain buffer salts, flavoring, coloring and sweetening agents as appropriate.

The compositions are formulated for parenteral administration by injection, e.g., by bolus injection or continuous infusion. Formulations for injection are presented in unit dosage form, e.g., in ampules or in multi-dose containers, with or without an added preservative. The compositions take such forms as suspensions, solutions or emulsions in oily or aqueous vehicles, and may contain formulatory agents such as suspending, stabilizing and/or dispersing agents. Alternatively, the active ingredient is in powder form for constitution with a suitable vehicle, e.g., sterile pyrogen-free water, before use. In general, water, a suitable oil, saline, aqueous dextrose (glucose), and related sugar solutions and glycols such as propylene glycol or polyethylene glycols are suitable carriers for parenteral solutions. Solutions for parenteral administration contain, for example, a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also citric acid and its salts and sodium ethylenediaminetetraacetic acid (EDTA) are optionally used. In addition, parenteral solutions optionally contain preservatives such as benzalkonium chloride, methyl- or propyl-paraben and chlorobutanol. Suitable pharmaceutical carriers are described in Remington: The Science and Practice of Pharmacy, 21st Edition, David B. Troy, ed., Lippicott Williams & Wilkins (2005), which is incorporated by reference in its entirety at least for the material related to pharmaceutical carriers and compositions.

The compositions are optionally formulated as a depot preparation. Such long acting formulations are optionally administered by implantation. Thus, for example, the compositions are formulated with suitable polymeric or hydrophobic materials (for example as an emulsion in an acceptable oil) or ion exchange resins, or as sparingly soluble derivatives, for example, as a sparingly soluble salt. The compositions are applied to or embedded with implants concurrent with or after surgical implant.

Additionally, standard pharmaceutical methods are employed to control the duration of action. These include control release preparations and appropriate macromolecules, for example, polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation are adjusted in order to control release. Optionally, the agent is incorporated into particles of polymeric materials such as polyesters, polyamino acids, hydrogels, poly (lactic acid) or ethylenevinylacetate copolymers. In addition to being incorporated, these agents are optionally used to trap the compound in microcapsules.

A composition for use in the methods described herein is optionally formulated as a sustained and/or timed release formulation. Such sustained and/or timed release formulations are made by sustained release means or delivery devices that are well known to those of ordinary skill in the art. The compositions are used to provide slow or sustained release of one or more of the active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable sustained release formulations are selected for use with the compositions described herein. Thus, single unit dosage forms suitable for oral administration, such as, but not limited to, tablets, capsules, gelcaps, caplets, powders, that are adapted for sustained release are used.

The compositions are optionally delivered by a controlled-release system. For example, the composition is administered using intravenous infusion, an implantable osmotic pump, liposomes, or other modes of administration. A controlled release system is placed in proximity to the target. For example, a micropump delivers controlled doses directly into bone, thereby requiring only a fraction of the systemic dose (see, e.g., Goodson, 1984, in Medical Applications of Controlled Release, vol. 2, pp. 115-138, which is incorporated by reference in its entirety at least for the material related to micropumps). In another example, a pharmaceutical composition is formulated with a hydrogel (see, e.g., U.S. Pat. Nos. 5,702,717; 6,117,949; 6,201,072, which are incorporated by reference in their entirety at least for the material related to hydrogels).

Optionally, it is desirable to administer the composition locally, i.e., to the area in need of treatment. For example, the composition is administered by injection into the bone marrow of a long bone, for example. Local administration is achieved, for example, by local infusion during surgery, topical application (e.g., in conjunction with a wound dressing after surgery), injection, catheter, suppository, or implant. An implant is of a porous, non-porous, or gelatinous material, including membranes, such as sialastic membranes, or fibers.

The pharmaceutical compositions described herein are administered by any conventional means available for use in conjunction with pharmaceuticals, either as individual therapeutic active ingredients or in a combination of therapeutic active ingredients. They are optionally administered alone, but are generally administered with a pharmaceutical carrier selected on the basis of the chosen route of administration and standard pharmaceutical practice.

The prostaglandins and prostaglandin receptor agonists described herein are provided in a pharmaceutically acceptable form including pharmaceutically acceptable salts and derivatives thereof. The term pharmaceutically acceptable form refers to compositions including the compounds described herein that are generally safe, relatively non-toxic and neither biologically nor otherwise undesirable. These compositions optionally include pharmaceutically acceptable carriers or stabilizers that are nontoxic to the cell or subject being exposed thereto at the dosages and concentrations employed. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (Uniqema, United Kingdom), polyethylene glycol (PEG), and PLURONICS™ (BASF, Germany).

The term pharmaceutically acceptable acid salts and derivatives refers to salts and derivatives of the prostaglandins and prostaglandin receptor agonists described herein that retain the biological effectiveness and properties of the prostaglandins and prostaglandin receptor agonists as described, and that are not biologically or otherwise undesirable. Pharmaceutically acceptable salts are formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The chemical stability of a composition comprising a prostaglandin or a pharmaceutically acceptable salt or ester thereof is enhanced by methods known to those of skill in the art. For example, an alkanoic acid ester of a polyethoxylated sorbitol (a polysorbate) is added to a composition containing a prostaglandin in an amount effective to enhance the chemical stability of the prostaglandin. Such a composition comprises one or more prostaglandins selected from the group of natural PGA, PGB, PGC, PGD, PGE, PGF or PGJ prostaglandins; or is selected from natural or synthetic derivatives or analogues thereof. Particularly preferred prostaglandins include the PGE series of prostaglandins as well as analogues and derivatives thereof.

The dosage administered is a therapeutically effective amount of the compound sufficient to result in promoting coupling between bone formation and bone resorption and varies depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

Toxicity and therapeutic efficacy of such compounds is determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it is expressed as the ratio LD50/ED50.

The data obtained from the cell culture assays and animal studies are optionally used in formulating a range of dosage for use in humans. The dosage of such compounds lies preferably within a range of circulating concentrations that include the ED50 with little or no toxicity. The dosage varies within this range depending upon the dosage form employed and the route of administration utilized. For any compound used in the provided methods, the therapeutically effective dose is estimated initially from cell culture assays. A dose is formulated in animal models to achieve a circulating plasma concentration range that includes the IC50 (i.e., the concentration of the test compound which achieves a half-maximal inhibition of symptoms) as determined in cell culture. Such information is used to more accurately determine useful doses in humans or other subjects. Levels in plasma are measured, for example, by high performance liquid chromatography.

The dosage ranges for the administration of the compositions are those large enough to produce the desired effect in which the symptoms of the disorder are affected. The dosage are not so large as to cause adverse side effects, such as unwanted cross-reactions and anaphylactic reactions. Dosage varies and is administered in one or more dose administrations daily for one or several days. For example, the pharmaceutical compositions comprising one or more prostaglandins and/or prostaglandin receptor agonists can be administered by systemic injection once or twice a day for one or several days. The compositions are administered daily as necessary for weeks, months or even years as necessary. Optionally the compositions are administered weekly or monthly. Thus, the compositions are administered once or more times daily for at least about 8 days, at least about 10 days, at least about 12 days, at least about 14 days, at least about 20 days, at least about 30 days or more or any number of days in between.

Kits

Also provided herein is a pack or kit comprising one or more containers filled with one or more of the ingredients (e.g., a prostaglandin, a prostaglandin receptor agonist, a prostaglandin derivative, a prostaglandin analog, Jagged1, etc.) described herein. Thus, for example, a kit described herein comprises one or more prostaglandins, one or more prostaglandin receptor agonists, one or more prostaglandin derivatives or analogs, Jagged1 or any combination thereof. Such kits optionally comprise solutions and buffers as needed or desired. The kit optionally includes an expanded population of stem cells made by the methods described above or can contain containers or compositions for making an expanded population of hematopoietic stem cells. Optionally associated with such pack(s) or kit(s) are instructions for use.

Also provided is a kit for providing an effective amount of a prostaglandin or prostaglandin receptor agonist or a combination thereof to increase HSCs in a subject comprising one or more doses of the prostaglandin or prostaglandin receptor agonist for use over a period of time, wherein the total number of doses of the prostaglandin or prostaglandin receptor agonist in the kit equals the effective amount of the prostaglandin or prostaglandin receptor agonist or combination thereof sufficient to increase HSCs in a subject. The period of time is from about one to several days or weeks or months. Thus, the period of time is from at least about 5, 6, 7, 8, 10, 12, 14, 20, 21 or 30 days or more or any number of days between one and 30. The doses of prostaglandin or prostaglandin receptor agonist or combination thereof are administered once, twice, three times or more daily or weekly. The kit provides one or multiple doses for a treatment regimen.

A kit for providing an effective amount of a prostaglandin or prostaglandin receptor agonist for expanding a population of HSCs is described. The kit comprises one or more doses of a prostaglandin or prostaglandin receptor agonists or combinations thereof for administration to HSCs or a mixture of HSCs and HSC supporting cells over a period of time, wherein the doses equal the effective amount of the prostaglandin or prostaglandin receptor agonist required to expand the population of HSCs. The period of time is from about one to several hours or one to several days. The dose of prostaglandin or prostaglandin receptor agonist or combination thereof is administered once, twice, three times or more daily or weekly and the kit provides one or multiple doses.

Optionally, the methods and kits comprise effective amounts of prostaglandins or prostaglandin receptor agonists for administering to the subject the prostaglandin or prostaglandin receptor agonist or combination thereof in a second or subsequent regime for a specific period of time. The second or subsequent period of time, like the first period of time, is, for example, at least one or more days, weeks or months, such as, for example, at least four, five, six, seven, eight, nine, ten, eleven, twelve, fourteen, twenty one, or thirty days or any number of days between. In the methods herein, the interval between the first treating period and the next treating period is optionally, for example, days, weeks, months or years. Thus, the interval between the first period of time and the next period of time is, for example, at least four, five, six, seven, eight, nine, ten, eleven, twelve, fourteen, twenty one, or twenty eight days or in number of days between. This treating schedule is repeated several times or many times as necessary. Such schedules are designed to correlated with repeated bone marrow depleting events such as repeated chemotherapy treatments or radiation therapy treatments. Optionally, a drug delivery device or component thereof for administration is included in a kit.

Disclosed are materials or steps in a method, compositions, and components that are used for, are used in conjunction with, are used in preparation for, or are products of the disclosed method and compositions. These and other materials are disclosed herein, and it is understood that when combinations, subsets, interactions, groups, etc. of these materials or steps are disclosed that, while specific reference of each various individual and collective combinations and permutation of these materials or steps may not be explicitly disclosed, each is specifically contemplated and described herein. For example, if a prostaglandin is disclosed and discussed and a number of modifications that can be made to a number of molecules including the prostaglandin are discussed, each and every combination and permutation of prostaglandin and the modifications that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Optional or optionally means that the subsequently described event or circumstance may or may not occur, and that the description includes instances where said event or circumstance occurs and instances where it does not.

Unless defined otherwise, all technical and scientific terms used herein have the same meanings as commonly understood by one of skill in the art to which the disclosed method and compositions belong. Publications cited herein and the material for which they are cited are hereby specifically incorporated by reference.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present application which will be limited only by the appended claims.

It is to be understood that the disclosed methods, compositions and kits are not limited to specific synthetic methods, specific analytical techniques, or to particular reagents unless otherwise specified, and, as such, may vary. Note the headings used herein are for organizational purposes only and are not meant to limit the description provided herein or the claims attached hereto.

EXAMPLES

Example 1

Prostaglandin E2 (PGE2) Expands Primitive Hematopoietic Cells In Vitro and In Vivo Materials and Methods Eight to ten week old FVB/N male mice were injected intraperitoneally once or twice daily for 16 days with either PGE2 (6 mg/kg body weight) or vehicle. Left hind limbs were harvested, fixed, decalcified, and processed. Right hindlimbs were harvested at the same time. The bone marrow was flushed and stained for FACS analysis with scal, ckit, and lineage marker antibodies.

UMR106 cells were grown in DMEM supplemented with 1.5 g/l sodium bicarbonate, 10% FBS, penicillin (100 U/ml), streptomycin (100 U/ml). After three days of growth the cells were 80% confluent and media was replaced with serum-free media. After 24 hr in serum-free media, PGE2 was added in noted concentrations. UMR 106 cells were treated with the Protein Kinase A (PKA) inhibitors H89 (0.5 hr prior to PGE2 treatment), and myristoylated PKI (0.5 hr prior to PGE2 treatment). Also used were cell-permeable cAMP analogs that activate cAMP dependent PKA n6 2'-0-dibutyryladenosine-3', 5'-cyclic monophpsphate (dibutyryl-cAMP) and 8-Bromoadenosine 3',5'-cyclic monophosphate (8-bromo).

At the designated times, total RNA and protein were harvested. Total RNA was extracted and analyzed by real time RT-PCR, normalizing for β-actin expression and t=0. Total protein was analyzed by Western blots performed using the XCELL SURELOCK™ system (Invitrogen, Carlsbad, Calif.). Blots were probed with Jag1 c-20 antibody (Santa Cruz Biotechnology, Inc., Santa Cruz, Calif.), and the loading control was B-actin.

Results

Figure 1B:
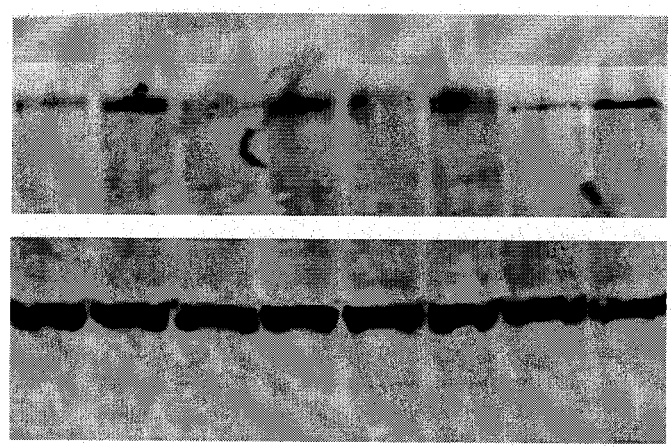
FIG. 1B is a Western blot showing total protein that was collected from both control and treated samples exposed to Jagged1 antibody, C20. Positive control (+ctr) was provided by HS27a cells, a human stromal cell line with high levels of Jagged1 protein, while HS5 cells from a human stromal cell line with minimal Jagged1 levels were used as a negative control.
Figure 2A:
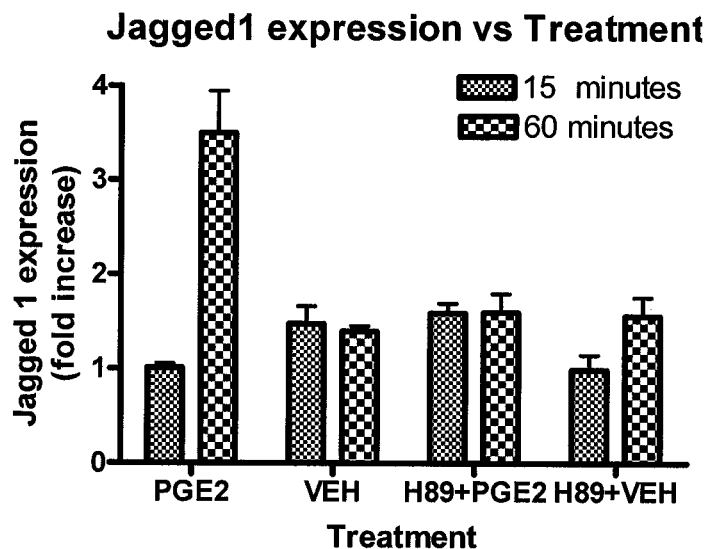
FIG. 2A is a graph showing that inhibition of PKA blocks PGE2-dependent increase of Jagged1 in UMR 106 cells. UMR106 cells were serum starved for 24 hours. They were pre-treated with H89 for 30 minutes followed by a single dose of PGE2 at $10^{-7}$ M or vehicle. RNA was collected from both control and treated samples to assess the fold change in Jagged1 RNA by real time RT-PCR analysis corrected for by β-actin.
Figure 2B:
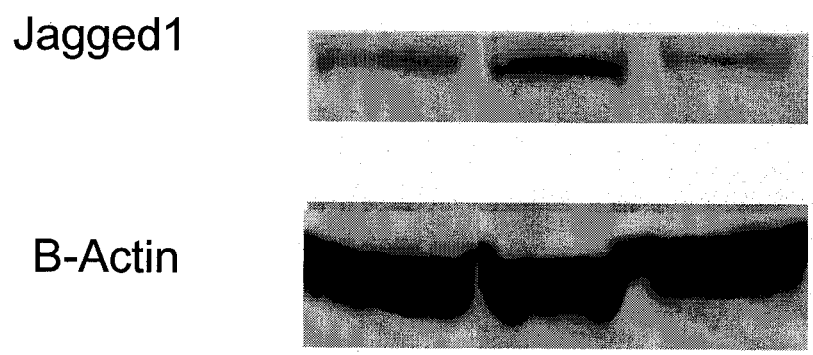
FIG. 2B shows the Western blot analysis. UMR106 cells were serum starved for 24 hours. They were pre-treated with Protein Kinase Inhibitor (PKI) at 200 µg/ml for one hour followed by a single dose of PGE2 at $10^{-7}$ M or vehicle. Total protein was collected from both PGE2 and vehicle treated samples for Western blot analysis with Jagged1 antibody C-20.
Figure 3:
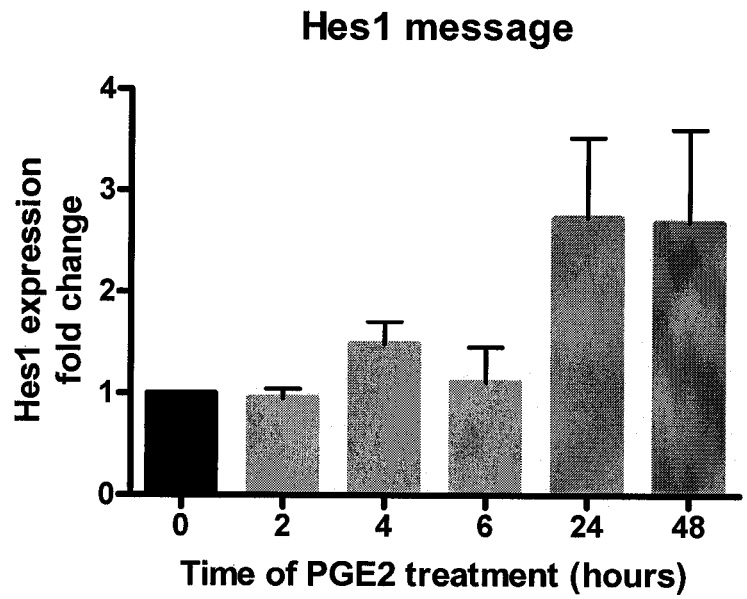
FIG. 3 is a graph showing that PGE2 treatment in UMR 206 cells increased expression of the Notch target gene HES1 as determined by real time RT-PCR analysis starting at 24 hours.
Figure 4:
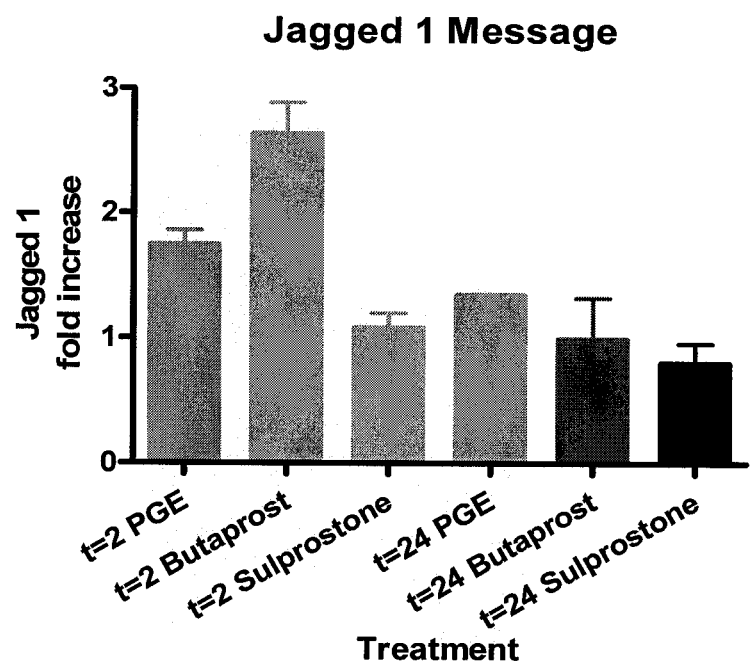
FIG. 4 shows EP-2 receptor's role in Jagged1 stimulation in osteoblastic cells. UMR 106 cells were treated with either butaprost (10 µM or $10^{-5}$M), a selective EP-2 receptor agonist; or sulprostone (1 µM or $10^{-6}$M), which activates both EP-1 and EP-3 receptors. Butaprost inhibited PGE2-induced Jagged1 expression suggesting that at least the EP2 receptor is important for the PGE2-dependent increase in Jagged1 expression.
Figure 5:
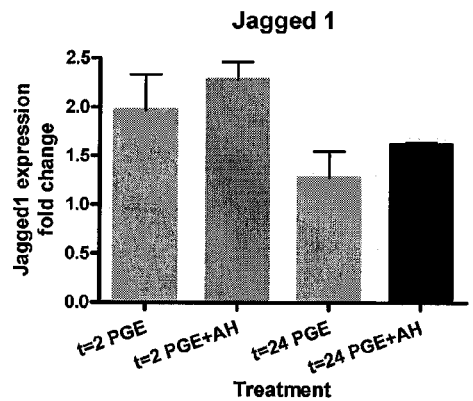
FIG. 5 is a graph showing that treatment of osteoblastic cells with AH23848, a selective EP4 receptor inhibitor, did not inhibit PGE2-induced expression of Jagged1. Osteoblastic cells were pretreated with AH23848 for 30 minutes with 30 µM or $3\times10^{-5}$M followed by PGE2 treatment.
Figure 6A:
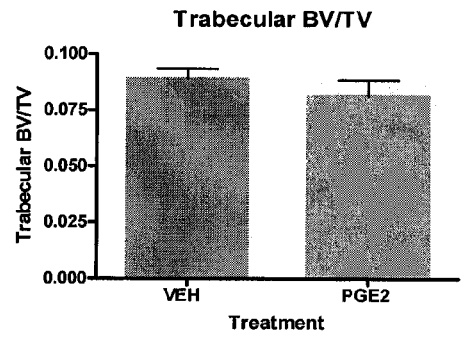
FIG. 6A is a graph showing quantification of bone volume performed by microCT analysis of femora from mice treated with PGE2 (6 mg/kg i.p. daily for 16 days (n=8)).
Figure 6B:
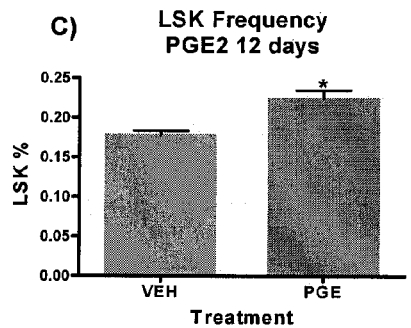
FIG. 6B is a graph showing an increase in HSCs as determined by flow cytometric analysis from femora and tibiae from the same mice as described in FIG. 6A. (*): $p<0.05$.
Figures 7A, 7B:
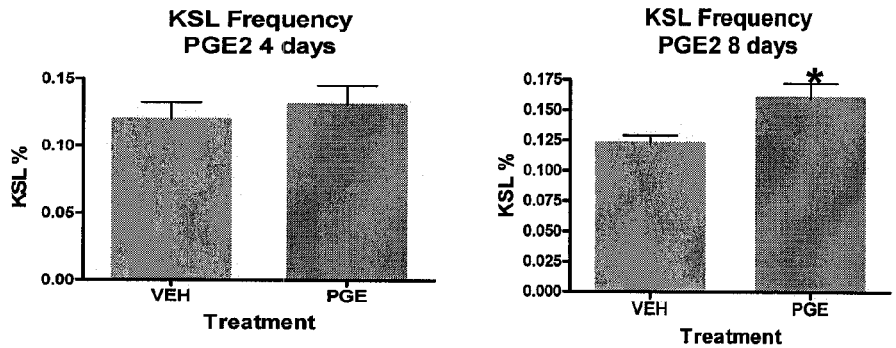
FIG. 7A is a graph showing KSL frequency at 4 days.
FIG. 7B is a graph showing KSL frequency at 8 days.

In the bone marrow, osteoblastic cells are a crucial component of the HSC niche. In particular, activation of the PTH/PTHrP receptor (PTHR1) in osteoblastic cells increases HSC frequency through Notch signaling. PTH (1-34) stimulates the Notch ligand Jagged1, which is sufficient for human HSC expansion in vitro. This stimulatory effect of PTH on Jagged1 is Protein Kinase A (PKA)-dependent, since it is blocked in the presence of the specific PKA inhibitors H89 and PKA Inhibitory Peptide (14-22) (PKI), and is reproduced by the direct PKA agonists 8-bromo-cAMP and dibutyryl-cAMP. To establish whether alternative PKA activators could also regulate osteoblastic Jagged1 and alter the HSC niche, PGE2 was utilized. PGE2 is a member of the prostaglandin family known to stimulate PKA. By real-time RT-PCR analysis, Jagged1 mRNA was increased up to 5 fold at 2 hours in UMR106 cells when treated with PGE2 ($10^{-7}$ M) compared to vehicle (FIG. 1A). Jagged1 protein was also increased after treatment with PGE2 (FIG. 1B). The PGE2-dependent Jagged1 increase was blocked in the presence of H89 and myristoylated PKA Inhibitory Peptide (14-22) (PKI) (200 µg/ml), demonstrating that PKA is necessary for osteoblastic Jagged1 stimulation by PGE2 (FIGS. 2A and 2B). Since systemic PGE2 has bone anabolic effects in both humans and animal models, adult wild-type FVB/N male mice were treated with PGE2 (6 mg/kg/day i.p.) for 16 days. At day 12, there was no significant increase in bone volume as measured by microCT analysis (FIG. 6A).

Figure 9:
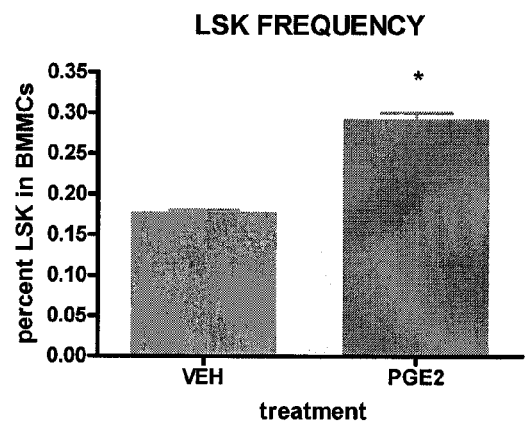
FIG. 9 is a graph showing the percent of HSCs in total bone marrow following in vivo administration of PGE2 in C57bl/6 mice. Eight to ten week old WT C5bl/6 mice given IP injections twice daily for 16 days of either 6 mg/kg PGE2 or vehicle (n=4 for each group). The left hind limb of each mouse was harvested, the bone marrow flushed out and the cells stained with lineage markers, sca-1 and c-kit. DAPI was used for a viability stain. The lin−, sca+, kit+ population was gated using FlowJo software for both PGE2 treated and vehicle treated samples. There was a 66% increase in lin−, sca+, kit+ (LSK) cells in PGE2 vs. vehicle treated mice (p=0.0093). As used herein, LSK and KSL frequency are used interchangeably.

In order to determine if the number of HSCs was increased in vivo by PGE2, eight to ten week old FVB/N mice were given daily IP injections for 16 days of either 6 mg/kg PGE2 or Vehicle. The left hind limb of each mouse was harvested, the bone marrow was flushed out, and the cells were stained with lineage markers, sca-1 and c-kit. DAPI was used for a viability stain. The lin−sca+ckit+population was gated using FlowJo software (FlowJo, Ashland, Oreg.) for both PGE2 treated and VEH treated samples. FIGS. 6B, 7A, 7B, 7C and 7D show that the percent of HSCs in total bone marrow was increased significantly as early as eight days of PGE2 administration. The same procedure was performed on C57bl/g mice. As shown in FIG. 9, the increase in HSCs reached 66% after 16 days of administration of PGE2 to C57bl/g mice. These data demonstrate that PGE2 increases HSCs in different strains of animals.

FIG. 8 is a graph showing that intermediate progenitors of hematopoietic stem cells are not increased by PGE2 treatment. Therefore, PGE2 specifically increases HSCs. The bone marrow mononuclear cells from mice were treated with vehicle and PGE2 to determine if there was an increase in intermediate progenitors in response to PGE2 using the colony forming unit-cell (CFU-C) assay. PGE2 did not increase colony forming unit cells. In addition, peripheral white blood cell and hematocrit levels were not changed in PGE2 vs. vehicle treated mice at 16 days (WBC counts: vehicle averaged 5.75±0.20×$10^3$/µl; PGE2 averaged 4.72±0.61×$10^3$/µl) (Hematocrit: vehicle averaged 42±1%; PGE2 averaged 43±2%) (n=6 for each treatment group). These data show that PGE2 specifically increases HSCs.

In summary, these data show that PGE2 increased Jagged1 expression and protein in a time dependent fashion in UMR106 osteosarcoma cells. Inhibition of PKA by H89 inhibited the PGE2-mediated Jagged1 message increase at 1 hr. Inhibition of PKA by PKI inhibited the PGE2-mediated increase in Jagged1 protein as early as 2 hours. PGE2 IP injections over 12 days had no significant effects on bone mineral volume in 8-10 week ole male mice. PGE2 IP injections over 8-16 days resulted in a significantly increased frequency of HSCs' from total bone marrow populations PGE2 increases expression and protein levels of the Notch ligand Jagged1 in UMR106 osteosarcoma cells. This action of PGE2 is mediated at least in part by activation of the cAMP-dependent/PKA signaling pathway, since dibutyryl-cAMP and 8-bromo cAMP are sufficient to increase Jagged1 and PGE2 is a known activator of PKA. Also H89 and PKI can inhibit Jagged1 expression.

In vivo treatment with PGE2 results in significantly increased cortical width of the tibia, as well as increased tibial metaphyseal trabecularization. PGE2 in vivo treatment also significantly increased the frequency of HSC's from total bone marrow populations when compared to vehicle.

Example 2

PGE2 Treatment In Vivo Does Not Increase Bone and Specifically Expands Short Term HSC (ST-HSC)

Since PGE2 production is increased in osteoblasts upon parathyroid hormone (PTH) treatment, PGE2 was used in the following experiments. Adult C57Bl/6 male mice were treated with PGE2 for 16 days. Analysis of the long bones from these mice demonstrated no evidence of a significant bone anabolic effect, either histologically or by micro-CT imaging (Calvi et al., *Blood* 108:30A (2006).

Figures 10A, 10B:
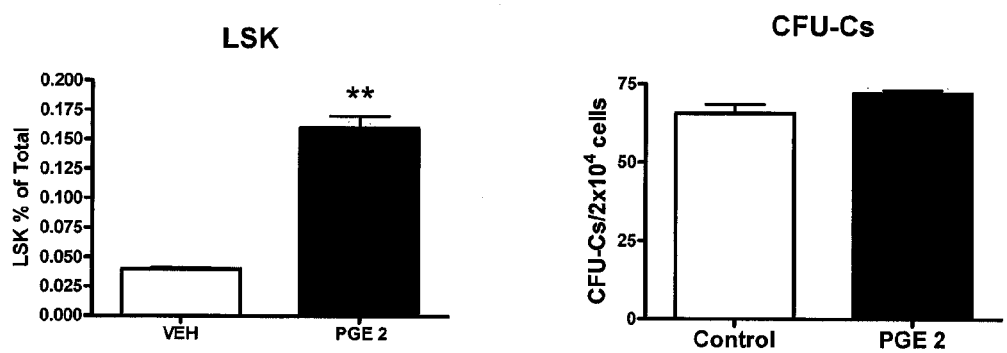
FIGS. 10A and 10B are graphs showing HSC frequency by flow cytometric analysis (FIG. 10A) and CFU-Cs (FIG. 10B), in vehicle vs PGE2 treated mice (n=8 per treatment group, **: p<0.01).

The opposite limb of the same mice was used for flow cytometric analysis, in vitro progenitor CFU-C assays and competitive repopulation. The HSC enriched LSK subpopulation of cells was significantly increased 3.5 fold (FIG. 10A), an effect superior to the PTH-dependent LSK increase. The BMMCs from this latter group were also tested for CFU-C activity in vitro. No evidence of PGE2 effects on CFU-C frequency was observed (FIG. 10B). Similarly, peripheral hematocrit, platelets and white blood cells were not changed in PGE2 vs. vehicle treated mice (WBC counts: vehicle: $5.75 \pm 0.20 \times 10^3/\mu l$, PGE2: $4.72 \pm 0.61 \times 10^3/\mu l$-Hematocrit: vehicle: $42 \pm 1\%$, PGE2: $43 \pm 2\%$ n=6 in each treatment group). These data show a PGE2-dependent specific expansion of HSCs, similar to the effects of PTH in vivo. A number of chemicals affecting prostaglandin synthesis as HSC regulators through a screen of 2498 compounds in zebrafish were identified (North et al., "A High-Throughput Chemical Genetic Screen in Zebrafish Establishes that Prostaglandin E2 is a Potent Regulator of Hematopoietic Stem Cell Formation, 4th International Society for Stem Cell Research Annual Meeting. Toronto, Canada, Jun. 28 to Jul. 3, 2006). The importance of PGE2 in HSC regulation was confirmed in zebrafish in vivo, and in murine BMMC ex vivo.

Figure 11A:
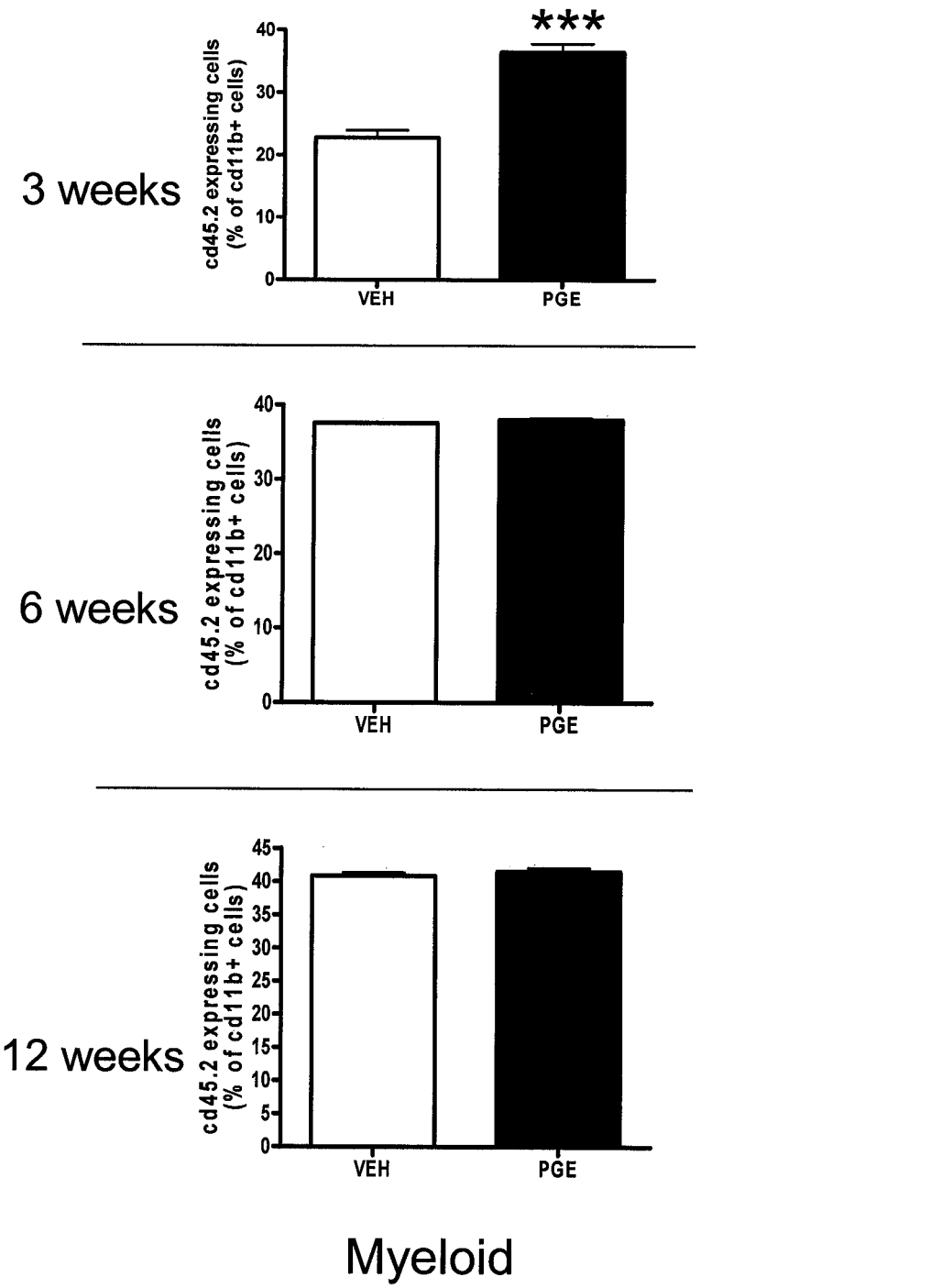
FIGS. 11A, 11B and 11C are graphs showing engraftment data from peripheral blood from competitive repopulation analysis from CD45.2+c57bl/6 mice treated daily with PGE2 (6 mg/kg i.p. twice daily) (n=8 mice per treatment group, n=10 recipient mice per group, 2 experiments). Similar results were achieved with 1:1 donor to recipient ratio. *=p<0.05; =p<0.01; *=p<0.001.
Figure 11B:
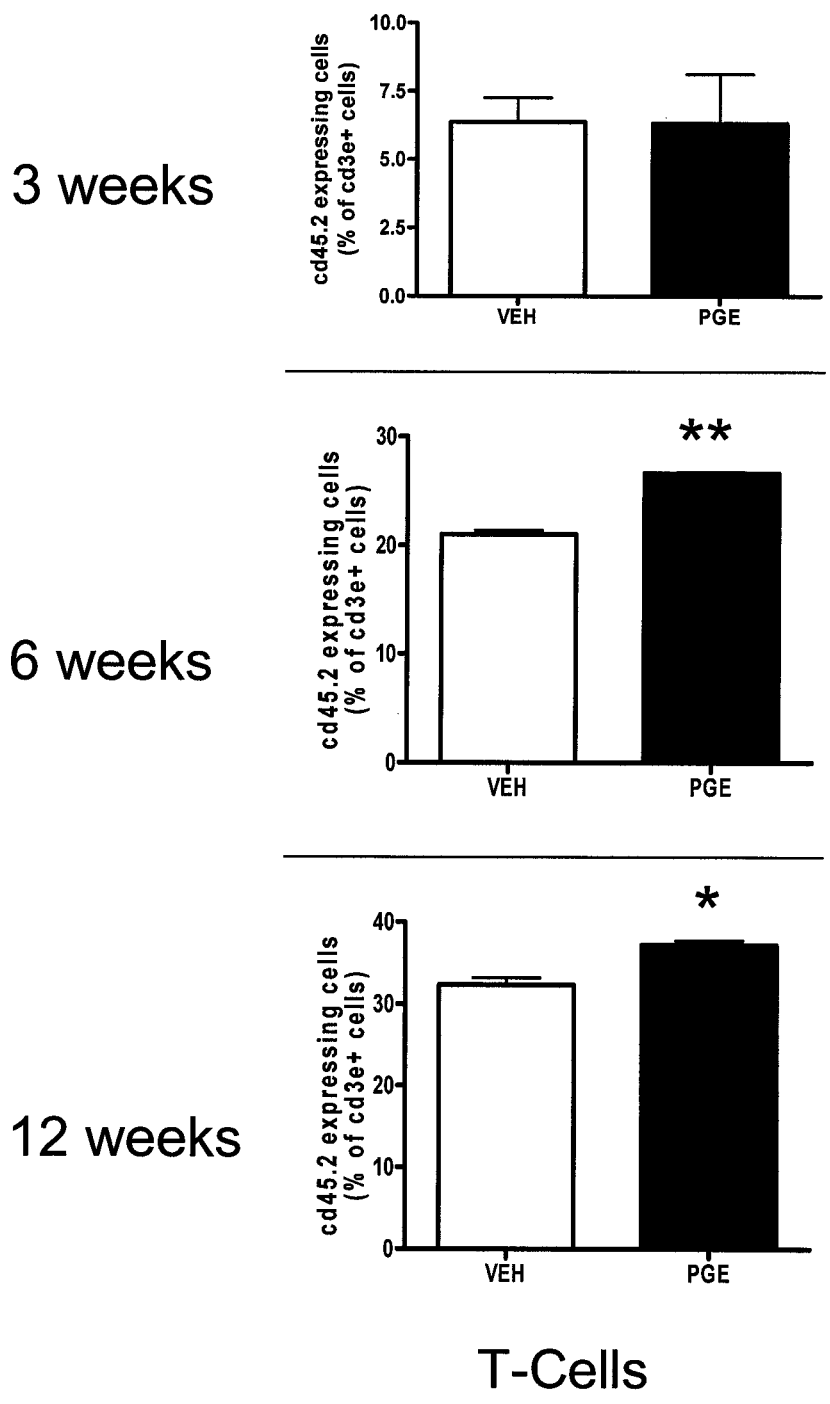
Figure 11C:
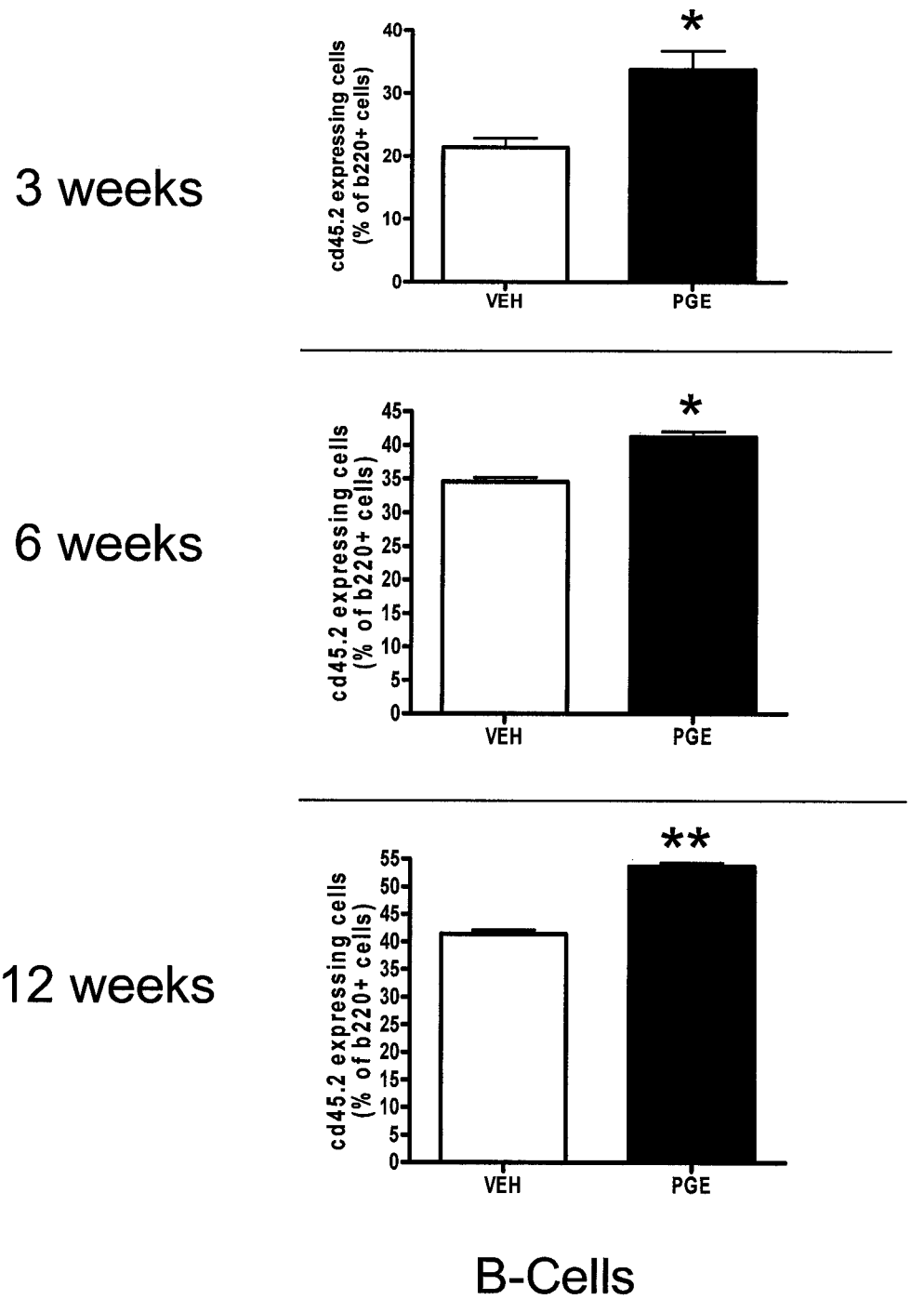

When competitive repopulation was performed with donor (CD45.2) bone marrow cells from either PGE2 or vehicle treated mice in a 1:2 ratio with competitor (CD45.1) bone marrow in lethally irradiated (CD45.1) recipients, PGE2 treated cells had superior multilineage reconstitution compared to vehicle treated HSC. This effect was limited to the short-term (up to 6 weeks) (FIGS. 11A, 11B and 11C), illustrating specific ST-HSC expansion. This is a unique in vivo model of selective ST-HSC increase. This effect is best illustrated by the short lived CD11b+myeloid subset (FIGS. 11A, 11B and 11C).

Thus, in vivo PGE2 treatment selectively expands short-term HSC (or ST-HSC), which have highly proliferative properties, but limited self-renewal.

Figure 12A:
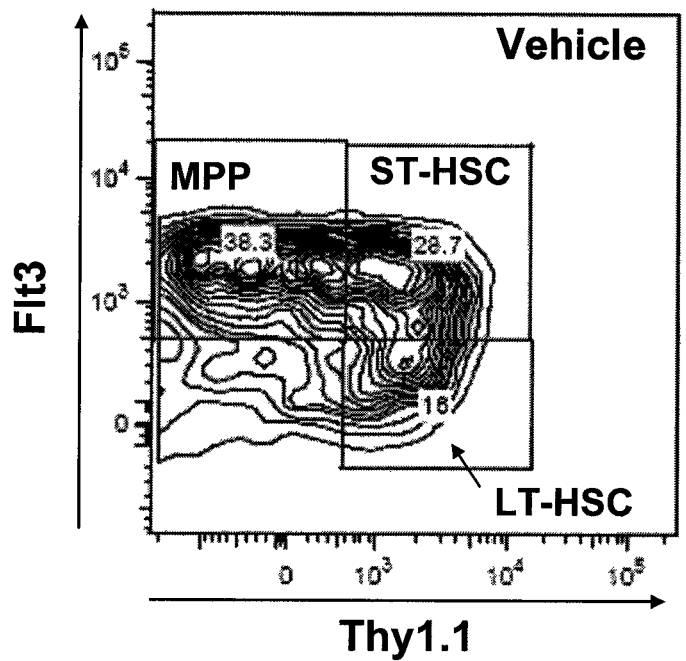
FIGS. 12A and 12B are representative plots of flow cytometric strategy of LSK subset from bone marrow of individual vehicle and PGE2-treated mice, numbers in the quadrant represent percentage of LSK.
Figure 12B:
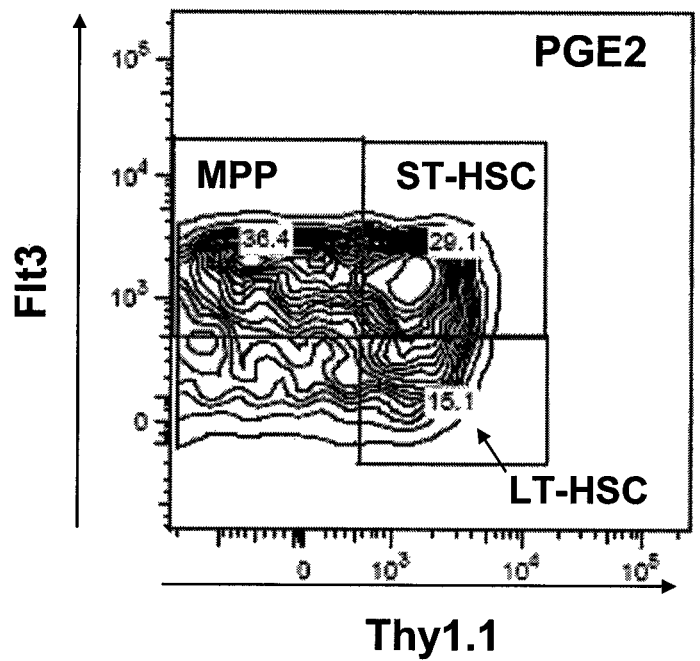

To further confirm this targeted PGE2 effect, LSK subset analysis based on Flt3 and Thy1.1 expression was performed. Consistent with the competitive repopulation data, PGE2 treatment significantly increased Flt3+Thy1.1int LSK ST-HSC as well as Flt3+Thy1.1-LSK Multipotent Progenitors, while there was no significant increase in Flt3-Thy1.1int LSK Long-Term HSC or LT-HSC compared to vehicle treatment (FIG. 12). Table 1 shows the quantification of HSC subsets from bone marrow of mice after vehicle or PGE2 treatment. (n=4 per treatment group).

TABLE 1

Quantification of HSC Subsets From Bone Marrow of Mice After Vehicle or Pge2 Treatment.

| HSC Subset | Vehicle-Treated | PGE2-Treated | p Value | p Value Summary |
|---|---|---|---|---|
| MPP | $0.0195 \pm 0.001323$ N = 4 | $0.0305 \pm 0.002398$ N = 4 | 0.007 | ** |
| ST-HSC | $0.0140 \pm 0.003082$ N = 4 | $0.02725 \pm 0.003568$ N = 4 | 0.0307 | * |
| LT-HSC | $0.007848 \pm 0.001190$ N = 4 | $0.01264 \pm 0.002233$ N = 4 | 0.1069 | NS |

MPP = Flt3 + Thy1.1- LSK.
ST-HSC = Flt3 + Thy1.1int LSK.
LT-HSC = Flt3 − Thy1.1int LSK.

ST vs LT-HSC activity can also be quantified by the in vivo clonogenic Colony Forming Unit-Spleen (CFU-S) assay, where day 8 CFU-S is closely associated with ST-HSC, while day 10-12 CFU-S are associated with LT-HSC activity. Consistent with a PGE2-dependent specific ST-HSC increase, BMMC from PGE2 treated mice gave rise to a significantly higher number of CFU-Sd8 compared to cells from vehicle-treated mice (10.5 vs 4.75 CFU-S per 60,000 BMMC, n=4 in each group, p=0.0053), while CFU-Sd10 were unchanged (12.5 vs 11.5 CFU-S per 60,000 BMMC, n=6, p=0.4950) (FIGS. 13A, 13B and 13C).

As shown in FIG. 11, PGE2 treatment in HSC donors dramatically increases myeloid cells at a time after bone marrow injury when neutropenia is most severe (days 0-15). Such timing suggests this may be an optimal strategy to mitigate hematopoietic injury by radiation. Moreover, since ST-HSC confer radioprotection, PGE2-dependent ST-HSC expansion would be expected to improve survival of lethally irradiated recipients receiving limiting numbers of BMMC from PGE2 vs vehicle-treated mice. To test this hypothesis, adult C57Bl/6 donor mice were treated with PGE2 or vehicle prior to bone marrow harvest. Recipient mice received myeloablative doses of radiation and suboptimal BMMC numbers (FIGS. 14A and 14B).

Figure 14A:
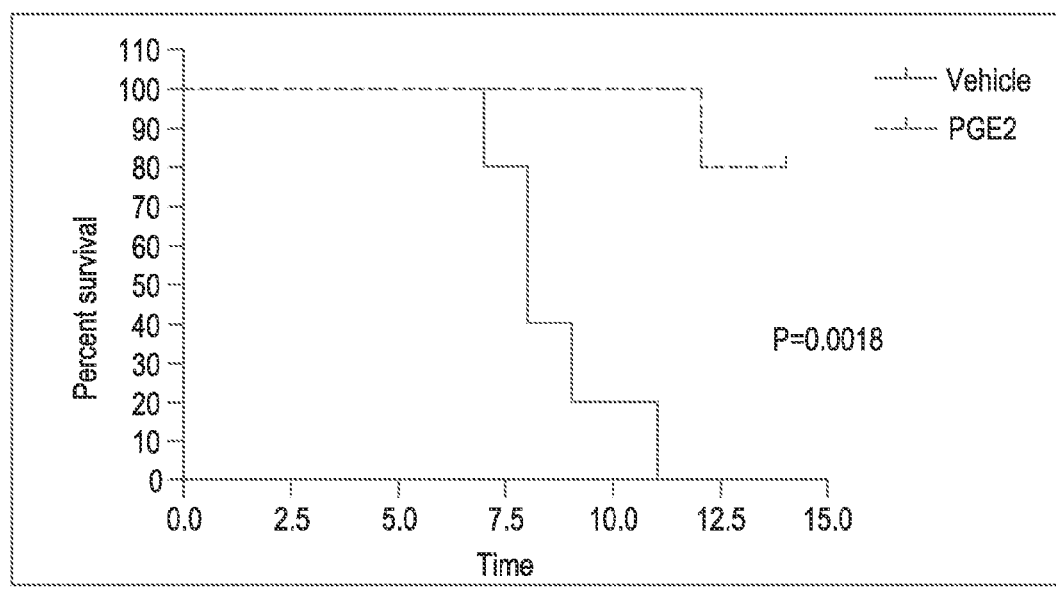
FIGS. 14A and 14B are graphs showing survival analysis by the method of Kaplan-Meyer in lethally irradiated recipients of suboptimal BMMC (1.5×10⁵ donor BMMC (A) and 0.75×10⁵ donor BMMC (B)) from vehicle or PGE2-treated donors. The graphs show that the effect depends on BMMC dose.
Figure 14B:
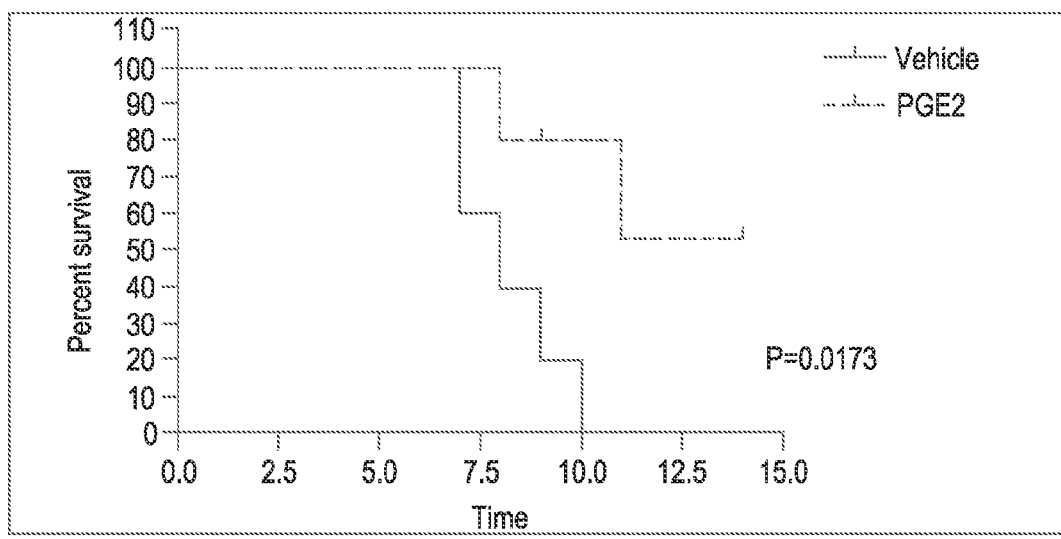

Recipients of BMMC from PGE2 treated mice had increased survival 30 days after transplantation compared to animals receiving BMMC from vehicle treated donors (150,000 donor cells: 80% vs 0% survival, p=0.0018; 75,000 donor cells: 53% vs 0% survival, p=0.0173) (FIGS. 14A and 14B). These data also suggest that PGE2 increases ST-HSC, which are less quiescent and more efficiently engraft in the short term.

Taken together, these data demonstrate specific PGE2-dependent regulation of ST-HSC. Moreover, these data indicate that selective therapeutic manipulation of ST-HSC can be exploited in clinical situations requiring rapid bone marrow reconstitution, such as in recovery from iatrogenic or pathologic myeloablative injury.

What is claimed is:

1. A method for selectively increasing the number of short-term hematopoietic stem cells (ST-HSC) in a mammalian subject comprising administering more than one dose of a prostaglandin EP-2 receptor agonist to the mammalian subject, to selectively increase the number of ST-HSCs in the subject, wherein the subject is a donor or a recipient of bone marrow transplant, and wherein the prostaglandin EP-2 receptor agonist is administered to the mammalian subject daily for several days.

2. The method of claim 1, wherein the subject is a human.

3. The method of claim 1, wherein the subject has a decreased blood cell level or is at risk for developing a decreased blood cell level as compared to a control blood cell level.

4. The method of claim 1, wherein the subject has anemia or blood loss.

5. The method of claim 1, wherein the subject is a bone marrow donor.

6. The method of claim 1, wherein the subject has depleted bone marrow.

7. The method of claim 1, wherein the prostaglandin EP receptor agonist is prostaglandin E2 (PGE2) or a derivative thereof.

8. The method of claim 7, wherein the prostaglandin EP receptor agonist is PGE2.

9. The method of claim 1, wherein the prostaglandin EP receptor agonist is PGE2.

10. The method of claim 1, wherein at least one dose of the prostaglandin EP-2 receptor agonist is administered to the mammalian subject before, at the same time, or after chemotherapy.

11. The method of claim 1, wherein at least one dose of the prostaglandin EP-2 receptor agonist is administered to the mammalian subject before, at the same time, or after radiation therapy.

12. The method of claim 1, wherein at least one dose of the prostaglandin EP-2 receptor agonist is administered to the mammalian subject before, at the same time, or after bone marrow harvest.

13. The method of claim 1, wherein at least one dose of the prostaglandin EP-2 receptor agonist is administered to the mammalian subject before, at the same time, or after bone marrow transplant.

14. The method of claim 1, wherein the prostaglandin EP-2 receptor agonist is administered one or more times daily for at least 5, 6, 7, or 8 days.

15. The method of claim 1, wherein the prostaglandin EP-2 receptor agonist is administered twice daily for at least 5, 6, 7, or 8 days.

16. The method of claim 1, wherein said prostaglandin EP-2 receptor agonist is administered to the subject before, at the same time, or after chemotherapy, radiation therapy, bone marrow harvest or a bone marrow transplant.

17. A method for selectively expanding a population of short-term hematopoietic stem cells (ST-HSCs) in a mammalian subject in vivo, comprising administering more than one dose of a prostaglandin EP-2 receptor agonist to an unexpanded population of hematopoietic stem cells (HSCs) or a mixture of HSCs and HSC supporting cells in the mammalian subject under conditions that allow the unexpanded population of HSCs to increase in number to form an expanded population of ST-HSCs, wherein the subject is a donor or a recipient of bone marrow transplant, and wherein the prostaglandin EP-2 receptor agonist is administered to the mammalian subject daily for several days.

18. The method of claim 17, wherein the prostaglandin EP receptor agonist is prostaglandin E2 or a derivative thereof.

19. The method of claim 17, wherein the prostaglandin EP receptor agonist is PGE2.

20. The method of claim 17, wherein the ST-HSCs are human ST-HSCs.

21. The method of claim 17, wherein the subject is a human.

22. The method of claim 17, wherein the subject has a decreased blood cell level or is at risk for developing a decreased blood cell level as compared to a control blood cell level.

23. The method of claim 17, wherein the subject has anemia or blood loss.

24. The method of claim 17, wherein the subject has depleted bone marrow.

25. The method of claim 17, wherein the prostaglandin EP receptor agonist is prostaglandin E2 or a derivative thereof.

26. The method of claim 17, wherein at least one dose of the prostaglandin EP-2 receptor agonist is administered to the mammalian subject before, at the same time, or after chemotherapy.

27. The method of claim 17, wherein at least one dose of the prostaglandin EP-2 receptor agonist is administered to the mammalian subject before, at the same time, or after radiation therapy.

28. The method of claim 17, wherein at least one dose of the prostaglandin EP-2 receptor agonist is administered to the mammalian subject before, at the same time, or after bone marrow harvest.

29. The method of claim 17, wherein at least one dose of the prostaglandin EP-2 receptor agonist is administered to the mammalian subject before, at the same time, or after bone marrow transplant.

30. The method of claim 17, wherein the prostaglandin EP-2 receptor agonist is administered one or more times daily for at least 5, 6, 7, or 8 days.

31. The method of claim 17, wherein the prostaglandin EP-2 receptor agonist is administered twice daily for at least 5, 6, 7, or 8 days.

32. The method of claim 17, wherein said prostaglandin EP-2 receptor agonist is administered to the subject before, at the same time, or after chemotherapy, radiation therapy, bone marrow harvest or a bone marrow transplant.

33. A method for selectively increasing the number of short-term hematopoietic stem cells (ST-HSC) in a mammalian subject comprising administering to said subject ONO-8815Ly or ONO-AE1-259 to selectively increase the number of ST-HSCs in said subject.

34. The method of claim 33 comprising administering to said subject ONO-8815Ly.

35. The method of claim 33 comprising administering to said subject ONO-AE1-259.

* * * * *